United States Patent
Yu et al.

(10) Patent No.: US 9,713,681 B2
(45) Date of Patent: Jul. 25, 2017

(54) METHOD AND NEBULIZATION MODULE PROVIDING CONSTANT ELECTRIC POWER BY AUTOMATIC COMPENSATION

(71) Applicant: HEALTH & LIFE CO., LTD., New Taipei (TW)

(72) Inventors: Shan-Yi Yu, New Taipei (TW); Wen-Yu Tsai, New Taipei (TW)

(73) Assignee: Health & Life Co., Ltd., New Taipei (TW)

( * ) Notice: Subject to any disclaimer, the term of this patent is extended or adjusted under 35 U.S.C. 154(b) by 440 days.

(21) Appl. No.: 14/505,377

(22) Filed: Oct. 2, 2014

(65) Prior Publication Data

US 2015/0202387 A1    Jul. 23, 2015

Related U.S. Application Data

(60) Provisional application No. 61/928,655, filed on Jan. 17, 2014.

(51) Int. Cl.
| | |
|---|---|
| *A61M 11/00* | (2006.01) |
| *A61M 15/00* | (2006.01) |
| *B06B 1/02* | (2006.01) |
| *B05B 17/06* | (2006.01) |

(52) U.S. Cl.
CPC ...... *A61M 11/005* (2013.01); *A61M 15/0085* (2013.01); *B06B 1/0253* (2013.01); *B06B 1/0284* (2013.01); *A61M 2205/0294* (2013.01); *A61M 2205/33* (2013.01); *A61M 2205/82* (2013.01); *B05B 17/0607* (2013.01); *B06B 2201/77* (2013.01)

(58) Field of Classification Search
CPC ............ A61M 11/005; A61M 15/0085; A61M 2205/82; A61M 2205/0294; A61M 2205/33; B06B 1/0253; B06B 1/0284; B06B 2201/77; B06B 17/0607
See application file for complete search history.

(56) References Cited

U.S. PATENT DOCUMENTS

| | | | |
|---|---|---|---|
| 6,142,146 A * | 11/2000 | Abrams | A61M 15/0085 128/203.15 |
| 2003/0192532 A1 | 10/2003 | Hopkins | |
| 2005/0178848 A1 | 8/2005 | Robbins | |
| 2009/0090361 A1 * | 4/2009 | Gumaste | A61M 15/0085 128/203.15 |
| 2010/0122696 A1 | 5/2010 | Weng et al. | |
| 2013/0269686 A1 | 10/2013 | Pezzano et al. | |

* cited by examiner

*Primary Examiner* — Steven Douglas
(74) *Attorney, Agent, or Firm* — Muncy, Geissler, Olds & Lowe, P.C.

(57) ABSTRACT

An ultrasonic nebulizer including a circuit unit, a nebulization module, and a frequency sweeping unit. Constant electric power in the nebulization module of the ultrasonic nebulizer is maintained by automatic compensation of electric power consumption and/or current consumption. A fixed current consumption and electric power consumption of the nebulization module of the ultrasonic nebulizer is achieved by auto compensation, thereby improving nebulization performance.

34 Claims, 3 Drawing Sheets

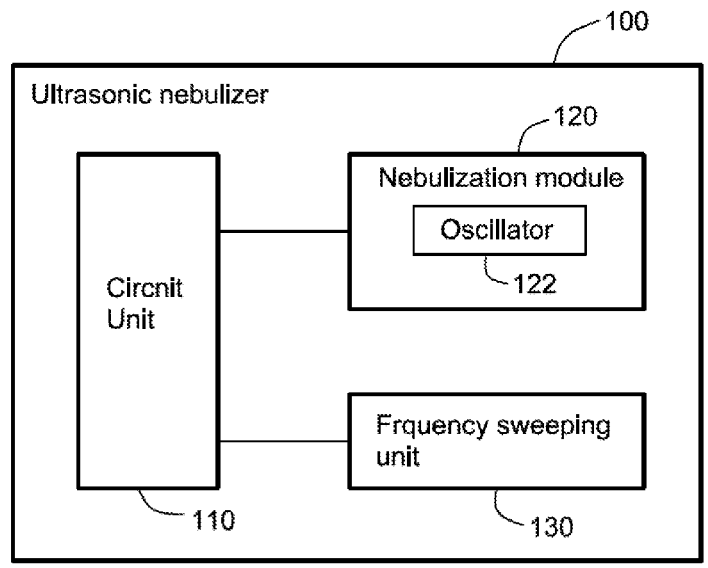

```
┌─ Ultrasonic nebulizer ──────────────────────── 100
│                                    ┌─ 120
│                        Nebulization module
│   ┌─────────┐         ┌─────────────────┐
│   │         │─────────│   Oscillator    │
│   │ Circuit │         │      └─ 122     │
│   │  Unit   │         └─────────────────┘
│   │         │
│   │         │         ┌─────────────────┐
│   │         │─────────│ Frquency sweeping│
│   │         │         │      unit        │
│   └─────────┘         └─────────────────┘
│      └─ 110                  └─ 130
└─────────────────────────────────────────────
```

FIG. 1

```
                            Start
                              │
                              ▼
        ┌─────────────────────────────────────────┐
        │ providing a circuit unit with a pre-    │
        │ determined electric power value (W)     │─── 210
        └─────────────────────────────────────────┘
                              │
                              ▼
        ┌─────────────────────────────────────────┐
        │ sending a voltage (V) from the circuit  │
        │ unit of the ultrasonic nebulizer to a   │─── 220
        │ nebulization module of the ultrasonic   │
        │ nebulizer                               │
        └─────────────────────────────────────────┘
                              │
                              ▼
        ┌─────────────────────────────────────────┐
        │ generating, by the frequency sweeping   │
        │ unit, an operating frequency range of   │─── 230
        │ the nebulization module                 │
        └─────────────────────────────────────────┘
                              │
                              ▼
        ┌─────────────────────────────────────────┐
        │ determining, by the frequency sweeping  │
        │ unit, a maximum current value (I) at a  │
        │ highest resonant frequency of the       │─── 240
        │ nebulization module by sweeping         │
        │ frequency in the operating frequency    │
        │ range                                   │
        └─────────────────────────────────────────┘
                              │
                              ▼
        ┌─────────────────────────────────────────┐
        │ sending, by the frequency sweeping      │
        │ unit, the maximum current value (I) to  │─── 250
        │ the nebulization module                 │
        └─────────────────────────────────────────┘
                              │
                              ▼
        ┌─────────────────────────────────────────┐
        │ adjusting the voltage (V) of the circuit│
        │ unit by multiplying a parameter (C) to  │
        │ return to the pre-determined electric   │─── 260
        │ power (W), wherein the parameter (C) is │
        │ obtained through the formula: W =       │
        │ (V x C) x I                             │
        └─────────────────────────────────────────┘
                              │
                              ▼
                            End
```

FIG. 2

```
                    ┌─────────┐
                    │  Start  │
                    └────┬────┘
                         ▼
    ┌────────────────────────────────────────────┐
    │ Providing a circuit unit with a pre-determined │──── 310
    │ electric power value (W)                   │
    └────────────────────┬───────────────────────┘
                         ▼
    ┌────────────────────────────────────────────┐
    │ Sending a voltage (V) from the circuit unit of the │
    │ ultrasonic nebulizer to a nebulization module of the │──── 320
    │ ultrasonic nebulizer                       │
    └────────────────────┬───────────────────────┘
                         ▼
    ┌────────────────────────────────────────────┐
    │ Generating, by the frequency sweeping unit, an │
    │ operating frequency range of the nebulization │──── 330
    │ module                                     │
    └────────────────────┬───────────────────────┘
                         ▼
    ┌────────────────────────────────────────────┐
    │ Determining, by the frequency sweeping unit, a │
    │ maximum current value (I) at a highest resonant │
    │ frequency of the nebulization module by frequency │──── 340
    │ sweeping in the operating frequency range  │
    └────────────────────┬───────────────────────┘
                         ▼
    ┌────────────────────────────────────────────┐
    │ Sending, by the frequency sweeping unit, the │
    │ maximum current value (I) to the nebulization │──── 350
    │ module                                     │
    └────────────────────┬───────────────────────┘
                         ▼
    ┌────────────────────────────────────────────┐
    │ Adjusting the voltage (V) of the circuit unit by │
    │ multiplying a parameter (C) to return to the pre- │
    │ determined electric power (W), wherein the │──── 360
    │ parameter (C) is obtained through the formula: W │
    │ = (V x C) x I                              │
    └────────────────────┬───────────────────────┘
                         ▼
                ╱ Determining wheher ╲ ──── 370
          Yes  ╱  a frequency sweeping ╲
    ◄────────⟨   period is expired ?   ⟩
               ╲                      ╱
                ╲                    ╱
                         │ No
                         ▼
                     ┌───────┐
                     │  End  │        FIG. 3
                     └───────┘
```

METHOD AND NEBULIZATION MODULE PROVIDING CONSTANT ELECTRIC POWER BY AUTOMATIC COMPENSATION

FIELD OF THE INVENTION

The invention relates to a nebulization module of an ultrasonic nebulizer. Particularly, the invention provides an ultrasonic nebulizer and a process for maintaining constant current consumption and/or constant electric power consumption of the ultrasonic nebulizer so that the electric power can be automatically compensated.

BACKGROUND OF THE INVENTION

Medical nebulizers for generating a fine spray or aerosol of a liquid medicine that can be inhaled by a patient are well known devices commonly used in the treatment of certain conditions and diseases. Nebulizers are used in treatments for conscious, spontaneously-breathing patients and for controlled ventilated patients.

An ultrasonic nebulizer uses an oscillation signal to drive a piezoelectric oscillator for producing mechanical vibration. The vibration energy is coupled to a liquid to be nebulized for producing capillary waves thereon and droplets. The ultrasonic nebulizer can be used for medication or producing droplet applications.

U.S. 20030192532 provides a nebulizer comprising an electrically energizable ultrasonic transducer having an oscillation frequency dependent current and voltage characteristic exhibiting the occurrence of a minimum magnitude of current through the transducer at an anti-resonance frequency of the transducer, the voltage across the transducer increasing with an increase in frequency within a range of frequencies including said anti-resonance frequency. U.S. 20050178848 provides a nebulization system, which creates a uniform fog of tiny suspended liquid droplets, to lubricate the surfaces of MEMS devices. U.S. 20100122696 discloses a method for adjusting an operation frequency of an ultrasonic nebulizer and checking an operating state of the ultrasonic nebulizer by detecting the current to determine a resonant frequency and whether the resonant frequency deviates from a predetermined normal range. U.S. 20130269686 relates to nebulizer assemblies configured to reduce or inhibit patient secretions or condensation from clogging or draining into a nebulizer, thus improving the function of the nebulizer.

However, the prior art faces the problem that in mass production of nebulization modules, it is difficult to ensure that the nebulization modules have similar electric power consumption; each may have different current consumption and electric power consumption. Moreover, since the nebulization module in a nebulizer is disposable, the inconsistent electric power consumption and current consumption may result in reducing efficiency of the nebulizer or increasing power consumption.

Therefore, there is a need to develop a nebulization module with automatically compensated electric power consumption.

SUMMARY OF THE INVENTION

In one aspect, the invention provides an ultrasonic nebulizer. The ultrasonic nebulizer comprises a circuit unit, a nebulization module, and a frequency sweeping unit. The circuit unit with a pre-determined electric power w is used for sending a voltage V. The nebulization module is used for receiving the voltage V from the circuit unit. The frequency sweeping unit is used for generating an operating frequency range of the nebulization module, sweeping frequency in the operating frequency range, determining a maximum current value I corresponding to a highest resonant frequency and sending the maximum current value I to the nebulization module. The voltage V sent from the circuit unit is adjusted by multiplying a parameter $\Delta C$ to achieve a pre-determined voltage, wherein the parameter is obtained through the formula: $W=(V\times\Delta C)\times I$.

In another aspect, the invention provides a process for maintaining constant electric power of an ultrasonic nebulizer, comprising the following steps: providing a circuit unit with a pre-determined electric power value W; sending a voltage V from the circuit unit of the ultrasonic nebulizer to a nebulization module of the ultrasonic nebulizer; generating, by a frequency sweeping unit, an operating frequency range of the nebulization module; determining, by the frequency sweeping unit, a maximum current value I at a highest resonant frequency of the nebulization module by sweeping frequency in the operating frequency range; sending, by the frequency sweeping unit, the maximum current value I to the nebulization module; and adjusting the voltage V of the circuit unit by multiplying a parameter $\Delta C$ in order to return to the pre-determined electric power W, wherein the parameter $\Delta C$ is obtained through the formula: $W=(V\times\Delta C)\times I$.

BRIEF DESCRIPTION OF THE DRAWINGS

The details of one or more embodiments of the disclosure are set forth in the accompanying drawings and the description below. Other features and advantages of the invention will be apparent from the description, drawings and claims.

FIG. 1 is a block diagram of an ultrasonic nebulizer 100 in accordance with one embodiment of the invention.

FIG. 2 is a flowchart illustrating a process 200 for maintaining constant electric power of an ultrasonic nebulizer in accordance with one embodiment of the invention.

FIG. 3 is a flowchart illustrating a process 300 for maintaining constant electric power of an ultrasonic nebulizer in accordance with another embodiment of the invention.

DETAILED DESCRIPTION OF THE INVENTION

Embodiments, or examples, of the invention illustrated in the drawings are now described using specific languages. It will nevertheless be understood that no limitation on the scope of the invention is thereby intended. Any alterations and modifications in the described embodiments, and any further applications of principles described in this document are contemplated as would normally occur to one of ordinary skill in the art to which the invention relates. Reference numbers may be repeated throughout the embodiments, but this does not necessarily require that feature(s) of one embodiment apply to another embodiment, even if they share the same reference number.

The invention utilizes the technique of maintaining constant electric power in a nebulization module of an ultrasonic nebulizer by automatic compensation of electric power consumption and/or current consumption. Using such a technique, the invention allows a fixed current consumption and electric power consumption of a nebulization module of an ultrasonic nebulizer by auto compensation, thereby improving nebulization performance.

FIG. 1 is a block diagram of an ultrasonic nebulizer 100 in accordance with one embodiment of the invention. Referring to FIG. 1, the ultrasonic nebulizer 100 comprises a circuit unit 110, a nebulization module 120, and a frequency sweeping unit 130. The nebulization module 120 comprises an oscillator 122. The functions of the aforementioned elements will be respectively explained below.

The circuit unit 110 is used for maintaining constant electric power by automatically compensating current and electric power consumption. In one embodiment, the circuit unit 110 can be implemented as a microcontroller (MCU). The MCU is a small computer on a single integrated circuit containing a processor core, memory, and programmable input/output peripherals and so on.

The circuit unit 110 is set with a pre-determined electric power w and used for sending a voltage V to the nebulization module 120. The pre-determined electric power W can be determined by persons having ordinary skill in the art based on actual needs/requirements.

The frequency sweeping unit 130 is used for generating an operating frequency range of the nebulization module 120. The frequency sweeping unit 130 sweeps frequency in the operating frequency range, determines a maximum current value I corresponding to a highest resonant frequency, and sends the maximum current value I to the nebulization module 120. In one embodiment, the operating frequency range ranges from 100-120 kHz. It should be noted that the highest resonant frequency is the frequency with the maximum current value in the operating frequency range.

In order to maintain constant electric power consumption in the nebulization module 120 of the ultrasonic nebulizer 100, the voltage V sent from the circuit unit 110 should be adjusted. The voltage V can be adjusted by multiplying a parameter $\Delta C$ to achieve a pre-determined voltage, and the parameter $\Delta C$ is obtained through the formula: $W=(V \times \Delta C) \times I$. The unit of W is watt, the unit of V is voltage, and the unit of I is ampere. In one embodiment, the pre-determined electric power W ranges from 0.2 to 2.0 watt.

Preferably, W ranges from 0.5 to 1.5, 0.5 to 1.4, 0.5 to 1.3, 0.5 to 1.2, 0.5 to 1.1, 0.5 to 1.0, 0.6 to 1.0, 0.7 to 1.0, 0.6 to 1.5, 0.7 to 1.5, or 0.8 to 1.5 watt.

In one embodiment, the ultrasonic nebulizer 100 may be used for medication or producing droplet application, and thus the ultrasonic nebulizer 100 may be disposed under a measuring glass of a medicine delivery apparatus. With the reduction of the medicine, the pressure among it also changes, and then the highest resonant frequency of the ultrasonic nebulizer 100 will change as well. Since the highest resonant frequency of the ultrasonic nebulizer 100 varies with time, the highest resonant frequency should be determined by sweeping frequency periodically. Specifically, in order to determine the maximum current value corresponding to the highest resonant frequency, the frequency sweeping unit 130 may periodically sweep frequency in the operating frequency range of the nebulization module 120 to determine the maximum current value at the highest resonant frequency for each period, wherein each period ranges from 15 to 30 seconds. Please note that the period can be determined by persons having ordinary skill in the art based on actual needs/requirements.

FIG. 2 is a flowchart illustrating a process 200 for maintaining constant electric power in an ultrasonic nebulizer in accordance with one embodiment of the invention. In this embodiment, the process is adapted for the ultrasonic nebulizer 100 of FIG. 1. Detailed steps of the process 200 of this embodiment are elaborated below with reference to each element of the ultrasonic nebulizer 100.

Referring to FIGS. 1 and 2, at step 210, a circuit unit 110 is provided with a pre-determined electric power value W. At step 220, a voltage is sent from the circuit unit 110 of the ultrasonic nebulizer 100 to a nebulization module 120 of the ultrasonic nebulizer 100. At step 230, the frequency sweeping unit 130 generates an operating frequency range of the nebulization module. At step 240, the frequency sweeping unit 130 determines a maximum current value I at a highest resonant frequency of the nebulization module 120 by sweeping frequency in the operating frequency range. At step 250, the frequency sweeping unit 130 sends the maximum current value I to the nebulization module 120. At step 260, the voltage V of the circuit unit 110 is adjusted by multiplying a parameter $\Delta C$ in order to return to the pre-determined electric power W, wherein the parameter $\Delta C$ is obtained through the formula: $W=(V \times \Delta C) \times I$. The unit of W is watt, the unit of V is voltage, and the unit of I is ampere.

FIG. 3 is a flowchart illustrating a process 300 for maintaining constant electric power in an ultrasonic nebulizer in accordance with another embodiment of the invention. In this embodiment, the process is adapted for the ultrasonic nebulizer 100 of FIG. 1. Detailed steps of the process 300 of this embodiment are elaborated below with reference to each element of the ultrasonic nebulizer 100.

Compared to the process 200 described with reference to FIG. 2, the process 300 in FIG. 3 includes steps 310, 320, 330, 340, 350, 360 and 370, wherein the first six of these steps are the same as steps 210, 220, 230, 240, 250, 260 and 270 in the process 200 in FIG. 2, and step 370 is different from the steps in the process 200 in FIG. 2.

The steps in FIG. 3 that are the same as the steps in FIG. 2 are omitted to be described here. At step 370, the frequency sweeping unit 130 determines whether a frequency sweeping period has expired or not. If not, the process 300 is complete. If yes, the process is returned to step 340, in which the frequency sweeping unit 130 determines a maximum current value I at a highest resonant frequency of the nebulization module 120 by sweeping frequency in the operating frequency range. In one embodiment, each period ranges from 15 to 30 seconds. As described above, with the reduction of the medicine, the pressure among it also changes, and then the highest resonant frequency of the ultrasonic nebulizer 100 will change as well. In order to determine the maximum current value corresponding to the highest resonant frequency, the frequency sweeping unit 130 should periodically sweep frequency in the operating frequency range of the nebulization module 120 to determine the maximum current value at the highest resonant frequency for each period.

The process and ultrasonic nebulizer of the invention can maintain constant electric power. Particularly, the invention provides a nebulization module that has constant electric power after the disposable nebulization module is changed. By maintaining constant electric power and current consumption of an ultrasonic nebulizer, the electric power of the ultrasonic nebulizer can be automatically compensated so that nebulization performance can be improved.

The above description includes exemplary steps, but these steps are not necessarily required to be performed in the order shown. Steps may be added, replaced, changed order, and/or eliminated as appropriate, in accordance with the spirit and scope of the invention. Accordingly, the scope of the invention should be determined with reference to the following claims, along with the full scope of equivalences to which such claims are entitled.

What is claimed is:

1. An ultrasonic nebulizer comprising:
   a circuit unit with a pre-determined electric power (W) for sending a voltage (V);
   a nebulization module for receiving the voltage (V) from the circuit unit; and
   a frequency sweeping unit for generating an operating frequency range of the nebulization module, sweeping frequency in the operating frequency range, determining a maximum current value (I) corresponding to a highest resonant frequency and sending the maximum current value (I) to the nebulization module,
   wherein the voltage (V) sent from the circuit unit is adjusted by multiplying a parameter ($\Delta C$) to achieve a pre-determined voltage, wherein the parameter is obtained through a formula: $W=(V \times \Delta C) \times I$, wherein W is measured in watts, V is measured in volts, and I is measured in amperes.

2. The ultrasonic nebulizer according to claim 1, wherein the frequency sweeping unit periodically sweeps frequency in the operating frequency range of the nebulization module to determine a maximum current value at a highest resonant frequency for each period.

3. The ultrasonic nebulizer according to claim 2, wherein each period ranges from 15 to 30 seconds.

4. The ultrasonic nebulizer according to claim 1, wherein the operating frequency range ranges from 100-120 kHz.

5. The ultrasonic nebulizer according to claim 1, wherein the pre-determined electric power ranges from 0.2 to 2.0 watt.

6. The ultrasonic nebulizer according to claim 5, wherein the pre-determined electric power ranges from 0.5 to 1.5 watt.

7. The ultrasonic nebulizer according to claim 6, wherein the pre-determined electric power ranges from 0.5 to 1.4 watt.

8. The ultrasonic nebulizer according to claim 7, wherein the pre-determined electric power ranges from 0.5 to 1.3 watt.

9. The ultrasonic nebulizer according to claim 8, wherein the pre-determined electric power ranges from 0.5 to 1.2 watt.

10. The ultrasonic nebulizer according to claim 9, wherein the pre-determined electric power ranges from 0.5 to 1.1 watt.

11. The ultrasonic nebulizer according to claim 10, wherein the pre-determined electric power ranges from 0.5 to 1.0 watt.

12. The ultrasonic nebulizer according to claim 11, wherein the pre-determined electric power ranges from 0.6 to 1.0 watt.

13. The ultrasonic nebulizer according to claim 12, wherein the pre-determined electric power ranges from 0.7 to 1.0 watt.

14. The ultrasonic nebulizer according to claim 6, wherein the pre-determined electric power ranges from 0.6 to 1.5 watt.

15. The ultrasonic nebulizer according to claim 7, wherein the pre-determined electric power ranges from 0.7 to 1.5 watt.

16. The ultrasonic nebulizer according to claim 8, wherein the pre-determined electric power ranges from 0.8 to 1.5 watt.

17. The ultrasonic nebulizer according to claim 1, wherein the nebulization module comprises an ultrasonic oscillator.

18. The ultrasonic nebulizer according to claim 1, wherein the circuit unit is implemented as a microcontroller.

19. A process for maintaining constant electric power of an ultrasonic nebulizer, comprising the following steps:
    providing a circuit unit with a pre-determined electric power value (W);
    sending a voltage (V) from the circuit unit of the ultrasonic nebulizer to a nebulization module of the ultrasonic nebulizer;
    generating, by a frequency sweeping unit, an operating frequency range of the nebulization module;
    determining, by the frequency sweeping unit, a maximum current value (I) at a highest resonant frequency of the nebulization module by sweeping frequency in the operating frequency range;
    sending, by the frequency sweeping unit, the maximum current value (I) to the nebulization module; and
    adjusting the voltage (V) of the circuit unit by multiplying a parameter ($\Delta C$) to return to the pre-determined electric power (W), wherein the parameter ($\Delta C$) is obtained through a formula: $W=(V \times \Delta C) \times I$, wherein W is measured in watts, V is measured in volts, and I is measured in amperes.

20. The process according to claim 19, further comprising periodically sweeping frequency in the operating frequency range of the nebulization module to determine a maximum current value at a highest resonant frequency for each period.

21. The process according to claim 20, wherein each period ranges from 15 to 30 seconds.

22. The process according to claim 19, wherein the operating frequency range ranges from 100-120 kHz.

23. The process according to claim 19, wherein the pre-determined electric power ranges from 0.2 to 2.0 watt.

24. The process according to claim 23, wherein the pre-determined electric power ranges from 0.5 to 1.5 watt.

25. The process according to claim 24, wherein the pre-determined electric power ranges from 0.5 to 1.4 watt.

26. The process according to claim 25, wherein the pre-determined electric power ranges from 0.5 to 1.3 watt.

27. The process according to claim 26, wherein the pre-determined electric power ranges from 0.5 to 1.2 watt.

28. The process according to claim 27, wherein the pre-determined electric power ranges from 0.5 to 1.1 watt.

29. The process according to claim 28, wherein the pre-determined electric power ranges from 0.5 to 1.0 watt.

30. The process according to claim 29, wherein the pre-determined electric power ranges from 0.6 to 1.0 watt.

31. The process according to claim 30, wherein the pre-determined electric power ranges from 0.7 to 1.0 watt.

32. The process according to claim 24, wherein the pre-determined electric power ranges from 0.6 to 1.5 watt.

33. The process according to claim 32, wherein the pre-determined electric power ranges from 0.7 to 1.5 watt.

34. The process according to claim 33, wherein the pre-determined electric power ranges from 0.8 to 1.5 watt.

* * * * *